United States Patent [19]

Berger et al.

[11] Patent Number: 5,780,639
[45] Date of Patent: Jul. 14, 1998

[54] SILICONE MONOMERS AND OLIGOMERS HAVING A CARBOXYL FUNCTIONAL GROUP THEREON

[75] Inventors: Abe Berger, Summit; Dennis L. Fost, Ringwood, both of N.J.

[73] Assignee: Mona Industries, Inc., Paterson, N.J.

[21] Appl. No.: 911,382

[22] Filed: Aug. 14, 1997

[51] Int. Cl.$^6$ ............................................... C07D 207/24
[52] U.S. Cl. ............................................... 548/110
[58] Field of Search ............................................... 548/110

[56] References Cited

PUBLICATIONS

CA 127: 331907 Silicone monomers containing a carboxyl group and their preparation. Berger et al., Oct. 21, 1997.

*Primary Examiner*—Joseph McKane
*Attorney, Agent, or Firm*—Franklyn Schoenberg; Norman E. Lehrer

[57] ABSTRACT

Organosilane and organosiloxane monomers are provided containing at least one carboxyl ester functional group represented by the formula:

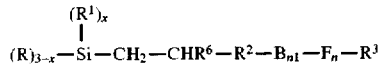

wherein:
R which can be the same or different are hydrolyzable groups;
$R^1$ which can be the same or different, are selected from substituted or unsubstituted alkyl, cycloalkyl, substituted or unsubstituted aryl, alkenyl, alkynyl or —OS$_i$ $(R^1)_3$;
x is zero to 3;
$R^2$ is linear or branched alkylene of 1–12 carbon atoms;
B is —NR$^6$, sulfur or oxygen;
$R^6$ is hydrogen or alkyl;
$n^1$ is zero or 1;
F is linear or branched alkylene of 1–10 carbon atoms;
n is zero or 1, with the proviso that if $n^1$ is 1, n is 1 and if $n^1$ is 0, n is 0;
$R^3$ is

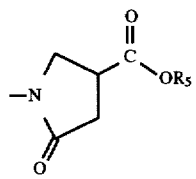

$R_5$ is alkyl or trialkylsilyl.

10 Claims, No Drawings

SILICONE MONOMERS AND OLIGOMERS HAVING A CARBOXYL FUNCTIONAL GROUP THEREON

FIELD OF THE INVENTION

The present invention relates to organosilane and organosilicone compounds and, more particularly, to novel organosilane compounds and organosiloxane compounds and oligomers containing a functional carboxyl group and to a method of making the same.

BACKGROUND OF THE INVENTION

Various organosilane and organosiloxane monomers or compounds including organosiloxane oligomers containing one or more organofunctional groups such as amines, vinyls, mercaptans, epoxies, halogens, and the like are widely known. These compounds have been used in a variety of ways such as coupling agents and adhesion promoters for inorganic materials, as reactants for modifying the properties of organic polymers, as crosslinking agents for curable organic polymer systems, as additives for a variety of home care and personal care compositions, as well as monomers for the preparation of silicon containing polymers.

While silane and siloxane monomers containing a variety of organofunctional groups are well known and can be readily prepared, organosilane and organosiloxane monomers containing functional carboxyl groups are generally not available commercially. Heretofore, no convenient method for preparing such monomers with carboxyl functional groups has been known and indirect procedures would generally have to be used for their preparation. Accordingly, the development of organosilane and organosiloxane monomers or compounds containing one or more organofunctional carboxyl groups and methods for readily preparing these compounds would be desirable. It would be particularly advantageous if methods for preparing such compounds not only employed readily available materials, but carboxyl-functional organosilicone monomers and oligomers could be prepared containing other functional groups as well, such as halogen groups, which makes possible the preparation of a variety of organosilicone derivatives including oligomers thereof.

While, as indicated, organosilane and organosiloxane compounds containing a variety of functional groups and methods for preparing the same, heretofore, have been known and used, there is no known disclosure or suggestion of the novel carboxyl-functional organosilane and organosiloxane compounds and oligomers of the present invention or of the method for making the same herein described.

SUMMARY OF THE INVENTION

It is accordingly an object of the present invention to provide a novel class of organosilane and organosiloxane compounds having at least one functional carboxylic ester group thereon and which may also include a variety of other functional groups as well.

It is another object of the present invention to provide a novel class of organosilane and organosiloxane compounds having a novel type of pyrrolidone-containing carboxylic ester functional group thereon and may also include other functional groups as well.

It is yet another object of the present invention to provide a novel class of organosiloxane compounds and oligomers having at least one functional carboxylic ester group thereon.

It is a further object of the present invention to provide a process for readily producing organosilane and organosiloxane compounds containing at least one carboxylic ester functional group.

These and other objects will become apparent from the description to follow.

In accordance with the present invention, there has now been discovered novel organosilane and organosiloxane compounds containing one or more functional carboxylic ester group(s) that may be represented by the following general formula:

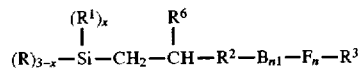

wherein:
R, which can be the same or different, are hydrolyzable groups such as but not limited to halogen, acyloxy, N,N-dialkylaminoxy, N-alkylamido, monoalkylamino, dialkylamino, isocyanato, alkylthio or cyano;

$R^1$ which can be the same or different, are substituted or unsubstituted alkyl, cycloalkyl, substituted or unsubstituted aryl, aralkyl, alkenyl, alkynyl or —O—Si—$(R^1)_3$;

x can be zero to 3;

$R^2$ is linear or branched alkylene of 1–12 carbon atoms, preferably methylene;

B is —$NR^6$, sulfur or oxygen;

$R^6$ is H or alkyl ($C_{1-20}$);

$n^1$ is zero or 1;

F is linear or branched alkylene of 1–10 carbon atoms, preferably ethylene;

n is zero or 1, with the proviso that if $n^1$ is 1, n is 1 and if $n^1$ is 0, n is 0;

$R^3$ is

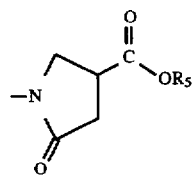

$R^5$ is alkyl ($C_{1-20}$) or trialkysilyl.

In another aspect of the present invention there are provided novel organosiloxane compounds and oligomers containing one or more functional carboxylic ester groups that may be represented by the formula:

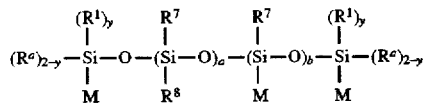

wherein:
$R^a$ which can be the same or different, are hydrolyzable groups such as but not limited to halogen, hydroxy, alkoxy, alkoxyalkoxy, acyloxy, N, N-dialkylaminoxy, N-alkylamido, monoalkylamino, dialkylamino, isocyanato, alkylthio or cyano;

$R^1$ are as hereinabove defined;

$R^7$ and $R^8$, which may be the same or different, are selected from alkyl, aryl, capped or uncapped polyoxyalkylene, alkaryl, aralkylene, alkenyl or alkynyl;

M can be the same or different and is selected from hydrogen, $R^a$, $R^1$ and —$CH_2$—$CHR^6$—$R^2$—$B_n{}^1$—$F_n$—$R^3$, with the proviso that at least one M is —$CH_2$—$CHR^6$—$R^2$—$B_n{}^1$—$F_n$—$R^3$;

y can be zero to 2;

a is from zero to 10;

b is from zero to 10;

$R^2$, $R^3$, $R^5$, B, F, n and $n^1$ are as defined hereinabove.

In yet another aspect of the present invention there is provided a method for preparing organosilane or organosiloxane monomers containing one or more pyrrolidone-containing functional carboxyl ester groups which comprises reacting a N-alkenyl pyrrolidone containing a carboalkoxyl group of the formula

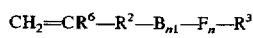

wherein:

$R^2$, $R^3$, $R^6$, F, B, $n^1$ and n are as hereinabove defined, with an organosilane hydride having one or more hydride groups of the formula

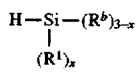

wherein:

$R^b$, which can be the same or different, are hydrolyzable groups such as but not limited to halogen, alkoxy, alkoxyalkoxy, acyloxy, N,N-Dialkylaminoxy, N-alkylamido, monoalkylamino, dialkylamino, isocyanato, alkylthio or cyano;

$R^1$ and x are as hereinabove defined.

at an elevated temperature (preferably between 65° C. and 130° C.) in the presence of a noble metal catalyst for a time sufficient to react the hydride group(s) on the silicon atom with the olefinic group on the pyrrolidone.

DESCRIPTION OF THE PREFERRED EMBODIMENTS

In accordance with the present invention there are provided novel organosilane and organosiloxane monomers or compounds containing a carboxylic ester functional group which may be represented by the general formula:

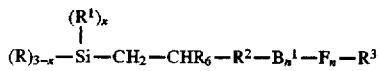

wherein:

R which can be the same or different, are hydrolyzable groups such as but not limited to halogen, acyloxy, N,N-Dialkylaminoxy, N-alkylamido, monoalkylamino, dialkylamino, isocyanato, alkylthio or cyano;

$R^1$ which can be the same or different, are substituted or unsubstituted alkyl, preferably lower alkyl ($C_1$-$C_6$); cycloalkyl, e.g. cycloheptyl; aralkyl, e.g. benzyl, phenylethyl etc.; substituted or unsubstituted aryl; alkenyl; alkynyl or —$OSi(R^1)_3$;

x can be zero to 3;

$R^2$ is linear or branched alkylene of 1-12 carbon atoms, preferably methylene;

B is —$NR^6$, sulfur or oxygen;

$R^6$ is H or alkyl ($C_{1-20}$), preferably hydrogen or methyl;

$n^1$ is zero or 1;

F is linear or branched alkylene of 1-10 carbon atoms, preferably ethylene;

n is zero or 1, with the proviso that if $n^1$ is 1, n is 1 and if $n^1$ is 0, n is 0;

$R^3$ is

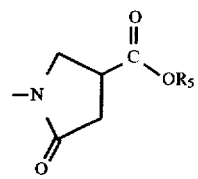

$R_5$ is alkyl ($C_{1-20}$), preferably lower alkyl ($C_{1-6}$) or trialkylsilyl.

In accordance with the present invention there are also provided organosiloxane compounds and oligomers containing one or more functional carboxyl groups that may be represented by the formula:

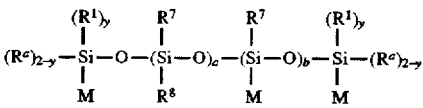

wherein:

$R^a$, which can be the same or different, are hydrolyzable groups such as but not limited to halogen, hydroxy, alkoxy, alkoxyalkoxy, acyloxy, N,N-dialkylaminoxy, N-alkylamido, monoalkylamino, dialkylamino, isocyanato, alkylthio or cyano;

$R^1$ which can be the same or different, are substituted or unsubstituted alkyl, cycloalkyl, substituted or unsubstituted aryl, aralkyl, alkenyl, alkynyl or —O—Si—$(R^1)_3$;

$R^7$ and $R^8$, which may be the same or different, are selected from alkyl, aryl, capped or uncapped polyoxyalkylene, alkaryl, aralkylene, alkenyl or alkynyl;

M can be the same or different and is selected from hydrogen, $R^a$, $R^1$ and —$CH_2$—$CHR_6$—$R^2$—$B_n{}^1$—$F_n$—$R^3$, with the proviso that at least one M group is —$CH_2$—$CHR^6$—$R^2$—$B_n{}^1$—$F_n$—$R^3$;

y can be zero to 2;

a is from zero to 10;

b is from zero to 10;

$R^2$, $R^3$, $R^5$, B, F, n and $n^1$ are as defined hereinabove.

The novel carboxylic ester functional organosilane and organosiloxane monomers of the present invention surprisingly and unexpectedly can be readily prepared by reacting a silane monomer having one or more hydride substituents on the silicon atom of the formula:

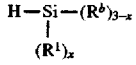

with a pyrrolidone nucleus containing a N-monosubstituted terminal olefinic group of the formula:

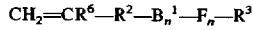

wherein:

$R^b$ which can be the same or different, are hydrolyzable groups such as but not limited to halogen, alkoxy, alkoxyalkoxy, acyloxy, N,N-Dialkylaminoxy, N-alkylamido, monoalkylamino, dialkylamino, isocyanato, alkylthio or cyano;

$R^1$ which can be the same or different, are substituted or unsubstituted alkyl, preferably lower alkyl ($C_1$–$C_6$); cycloalkyl, e.g. cycloheptyl; aralkyl, e.g. benzyl, phenylethyl etc.; substituted or unsubstituted aryl; alkenyl; alkynyl or —OSi($R^1$)$_3$;

x can be zero to 3;

$R^2$ is linear or branched alkylene of 1–12 carbon atoms, preferably methylene;

B is —$NR^6$, sulfur or oxygen;

$R^6$ is H or alkyl ($C_{1-20}$); preferably hydrogen or methyl;

$n^1$ is zero or 1;

F is linear or branched alkylene of 1–10 carbon atoms, preferably ethylene;

n is zero or 1, with the proviso that if $n^1$ is 1, n is 1 and if $n^1$ is 0, n is 0;

$R^3$ is

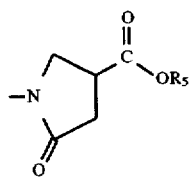

$R^5$ is alkyl, preferably lower alkyl ($C_{1-6}$) or trialkylsilyl.

The reaction is carried out in the presence of a noble metal (Group VIII metal) catalyst, preferably soluble platinum, at an elevated temperature (65° C. to 130° C.) for a time sufficient for substantially all of the N-alkenyl carboalkoxy containing pyrrolidone to react with the hydride group(s).

The reaction can be carried out neat or in inert solvents such as toluene, benzene, chlorobenzene, heptane and the like. In general, from about 0.5, preferably from about 0.9 to 1.1 equivalents of the N-alkenyl carboalkoxy containing pyrrolidone groups per functional hydride groups is reacted with the hydride groups of the silane monomer, wherein substantially all the N-alkenyl carboalkoxy containing pyrrolidone and, preferably all of the functional hydride group (s) are reacted and an organosilane or organosiloxane compound with at least one pyrrolidone-containing functional-carboxylic ester group(s), is formed. The reaction is carried out in the presence of a noble metal catalyst. Suitable platinum catalysts include solubilized platinum or platinum metal on supports such as alumina, charcoal and the like. In general from about $10^{-3}$ to $10^{-6}$ moles of platinum per mole of hydride group can be used.

The carboalkoxy containing pyrrolidone reactant suitable for use in accordance with the practice of the present invention may be prepared by the reaction of an olefinic amine having a functional primary amine group(s) of the formula:

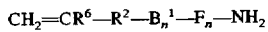

wherein:

$R^2$ is linear or branched alkylene of 1–12 carbon atoms, preferably methylene;

B is —$NR^6$, sulfur or oxygen;

$R^6$ is H or alkyl, preferably hydrogen or methyl;

F is linear or branched alkylene 1–10 carbon atoms, preferably ethylene;

n is zero or 1; and $n^1$ is zero or 1, with the provisio that if $n^1$ is 1, n is 1 and if $n^1$ is 0, n is 0;

with up to about one equivalent, preferably about stoichiometric quantities, of itaconic ester per primary amine group at an elevated temperature for a time sufficient for substantially all of the itaconic ester to react with the primary amine group(s) and the formation of pyrrolidone containing a carboalkoxyl functional group(s).

Itaconic acid (methylene succinic acid) and/or ester is a compound of the formula:

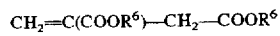

wherein $R^6$, which can be the same or different, is hydrogen or alkyl ($C_{1-20}$) preferably lower alkyl (1–6 carbon atoms).

The compound itaconic acid is available commercially from Pfizer Chemicals Division and Rhone Poulenc whereas ester derivatives thereof are available from Morflex, Inc., Greensboro, N.C. The compounds are produced by known fermentation techniques although chemical synthesis methods are also known.

Olefinic amine compounds suitable for use are any olefinic amines including diamines having at least one primary amine group of the formula:

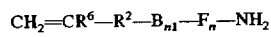

wherein, $R^2$, $R^6$, B, F, n and $n^1$ are as hereinabove defined.

Exemplary suitable allyl amine compounds include allyl amine, methallyl amine, allyloxypropyl amine, allylthiopropyl amine, methallyloxypropyl amine and exemplary suitable allyl diamine compounds are N-allyl ethylene diamine, N-allyl propylene diamine and N-allyl, N-methylene propylene diamine.

In general, from about 0.5, preferably from about 0.9 to about 1.1, equivalents of itaconic ester per functional primary amine group is reacted with the primary amine group of the olefinic amine compound wherein substantially all of the itaconic and preferably all the primary amine group(s) are reacted and an N-alkenyl carboalkoxy compound containing a pyrrolidone nucleus is formed of the formula:

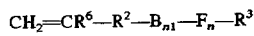

wherein $R^2$, $R^6$, B, F, $R^3$, $n^1$ and n are as defined hereinabove.

The reaction can be carried out neat or in an inert solvent such as alcohol, hydrocarbon solvent, chlorinated hydrocarbon and the like, as desired, in general at elevated temperatures up to about 175° C., preferably from about 90° C. to about 130° C. The reaction readily proceeds and generally complete reaction of the itaconic ester with the available primary amine group(s) occurs in the Michael Addition manner with the double bond of the itaconic ester followed by immediate cyclization to form a pyrrolidone group which will occur in from about 1 to 5 hours.

In another aspect of the present invention, the novel organosiloxane compounds and oligomers of the present invention can be readily prepared by reacting an organosiloxane compound or oligomer having one or more hydride groups on the silicone atoms of the forumla:

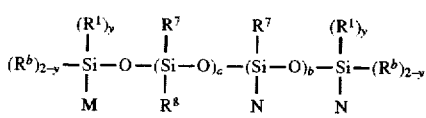

wherein:

- $R^b$, which can be the same or different, are hydrolyzable groups such as but not limited to halogen, alkoxy, alkoxyalkoxy, acyloxy, N,N-dialkylaminoxy, N-alkylamido,monoalkylamino, dialkylamino, isocyanato, alkylthio or cyano;
- $R^1$ which can be the same or different, are substituted or unsubstituted alkyl, cycloalkyl, substituted or unsubstituted aryl, aralkyl, alkenyl, alkynyl or —O—Si—$(R^1)_3$
- $R^7$ and $R^8$, which may be the same or different, are selected from alkyl, aryl, capped or uncapped polyoxyalkylene, alkaryl, aralkylene, alkenyl or alkynyl;
- N can be the same or different and is selected from hydrogen, $R^b$ and $R^1$, with the proviso that at least one N is hydrogen;
- y can be zero to 2;
- a is from zero to 10;
- b is from zero to 10;

With an ester containing pyrrolidone nucleus containing a N-monosubstituted terminal olefinic group as hereinabove described. The reaction is carried out as hereinabove described in the presence of a noble metal (Group VIII metal) catalyst, preferably soluble platinum, at an elevated temperature (65° to 130° C.) for a time sufficient for substantially all of the N-alkenylcarboalkoxy containing pyrrolidone to react with the hydride group(s).

The organosilicone monomers according to the present invention are useful, for example, as coupling agents and adhesion promoters for inorganic materials, as reactants for modifying the properties of organic polymers, as crosslinking agents for curable organic polymers, as additives for personal and home care products, as precursors for organic or organosilicone polymers of varying molecular weights and the like.

The above is a general description of the present invention. The following examples are given for the purpose of illustration and are not intended in any way to limit the invention as claimed. Unless noted to the contrary, proportions are on a weight basis.

EXAMPLE 1

This example illustrates the method for making N-allyl-4-carbomethoxy pyrrolidone.

A solution of 158 grams of Dimethyl itaconate and 200 ml of methanol is charged to a reaction vessel and 57 grams of allyl amine is added dropwise to the itaconate solution with agitation in the reaction vessel. During addition of allyl amine to the reaction mixture, the temperature increased from ambient to 62° C.

Upon complete addition of the allyl amine the reaction mixture is kept at reflux for 4 additional hours. The methanol is distilled from the reaction mixture and the reaction product is distilled at 115° C. under reduced pressure (1 mm). A yield of 92% is obtained. The structure of the reaction product is evaluated by IR.

EXAMPLE 2

This example illustrates the preparation of N-(Dimethyl chlorosilylpropyl)-4-carbomethoxy pyrrolidone.

To 183 grams of N-allyl-4-carbomethoxy pyrrolidone prepared as described in Example 1 and 1 ml of 0.1N chloroplatinic acid in isopropanol charged to a reaction vessel with agitation, 94.5 grams of Dimethyl chlorosilane is added dropwise to the reaction mixture and an exotherm occurs increasing the reaction mixture temperature to 90°–95° C. The reaction temperature is maintained at 95° C. for 4 hours after all the silane reactant is added to the reaction mixture. A colorless oil is obtained by distilling at 168°–170° C. under 2 mm pressure with about 90% yield. The structure of the reaction product is confirmed by NMR and IR.

EXAMPLE 3

This example illustrates the preparation of N-(Dichloromethylsilypropyl)-4-Carbomethoxy pyrrolidone.

A reaction mixture of 183 grams of N-allyl-4-carbomethoxy pyrrolidone prepared as described in Example 1 and 1 ml of 0.1N chloroplatinic acid in isopropanol is charged to a reaction vessel. 115 grams of methyldichlorosilane is added dropwise to the reaction mixture with agitation during which an exothermic reaction occurs increasing the temperature of the reaction mixture to 90°–95° C. The temperature of the reaction mixture is maintained at 95° C. for 4 hours after the addition of the silane is completed. The reaction mixture is distilled during which a colorless oil is obtained at a temperature of 174°–176° C. under 2 mm pressure. A yield of product of 93% is obtained and the structure is confirmed by IR and NMR.

EXAMPLE 4

This example illustrates the preparation of N-(Triacetoxysilylpropyl)-4-carbomethoxy pyrrolidone.

A reaction mixture is prepared from 183 grams of N-allyl-4-carbomethoxy prepared as described in example 1 and 1 ml of 0.1N chloroplatinic acid in a reaction vessel. 206 grams of triacetoxysilane is added dropwise to the reaction during which an exotherm is created increasing the reaction mixture to 110°–115° C. After all the silane reactant has been added, the temperature of the reaction mixture is maintained at 110° C. for 3 hours. A low melting reaction product is recovered from the solid reaction vessel and the structure of the product is confirmed by NMR and IR.

EXAMPLE 5

This example illustrates the preparation of N-[Bis(methyl ethylketoximino) methylsilylpropyl]-4-carbomethoxy pyrrolidone.

A reaction mixture is charged to a reaction vessel containing equal molar amounts of Bis(methyl ethyl ketoximino) methyl silane and N-allyl-4-carbomethoxy pyrrolidone and about $10^{-4}$ moles of chloroplatinic acid in isopropanol. The reaction mixture forms an exotherm of about 110° C. after which the reaction mixture is maintained at 130° C. for 3 hours. The structure of the reaction product is confirmed by NMR and IR.

EXAMPLE 6

This example illustrates the preparation of N-(Trichlorosilylpropyloxy propyl)-4-carbomethoxy pyrrolidone.

A reaction mixture of 236 grams of N-allyloxypropyl-4-carbomethoxy pyrrolidone prepared by replacing allyl amine with allyloxypropyl amine as described in Example 1. 0.1N chloroplatinic acid and isopropanol is charged to a reaction vessel and heated to about 85° C. 135.5 grams of Trichlorosilane is added dropwise to the reaction mixture with agitation. The reaction mixture is exothermic and heat is removed to maintain the temperature at about 90°–95° C. Upon adding all the trichlorosilane, the reaction temperature is maintained at 120° C. for 2 hours. Low boiling is materials are stripped from the reaction mixture under reduced pressure. A yield of 95% of product is obtained and the structure of the reaction product is confirmed by I.R. and NMR.

EXAMPLE 7

The addition of methyldichlorosilane to N-(allylthiopropyl)-4-carbomethoxy pyrrolidone in the presence of catalytic amounts of chloroplatinic acid results in the formation of N-(methyldichlorosilylpropylthiopropyl)-4-carbomethoxy pyrrolidone with yields and structure confirmed by G.C. analysis, I.R. and NMR.

EXAMPLE 8

Allyl methyl amine is cyanoethylated with acrylonitrile followed by palladium catalyzed reaction with hydrogen to prepare the reaction product N-allyl, N-methyl, propylene diamine is identified by NMR and I.R.

Equimolar amounts of N-allyl, N-methyl, propylene diamine prepared as described above and Dimethyl Itaconate are charged to a reaction vessel and heated slowly with agitation to 130°–150° C. After the exotherm subsides, the reaction mixture is maintained at 140° C. for 3 hours. The reaction product 1-(N-allyl, N-methyl aminopropyl)-4-carbomethoxy pyrrolidone is isolated by distillation.

Triethoxysilane is added dropwise to an equimolar amount of the 1-(N-allyl, N-methyl aminopropyl)-4-Carbomethxyl pyrrolidone prepared above in the presence of 0.1M chloroplatinic acid while maintaining a reaction temperature of 120°–140° C. After completion of the reaction, the product is isolated by fractionation of the reaction mixture and the product is identified by NMR and I.R.

What is claimed is:

1. Organosilane and organosiloxane monomers having at least one carboxylic ester funtional group that is represented by the formula:

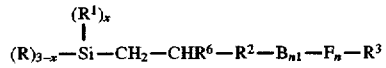

wherein:

R which can be the same or different are hydrolyzable groups;

$R^1$ which can be the same or different, are selected from substituted or unsubstituted alkyl, cycloalkyl, substituted or unsubstituted aryl, alkenyl, alkynyl or —OSi$(R^1)_3$;

x is zero to 3;

$R^2$ is linear or branched alkylene of 1–12 carbon atoms;

B is —NR$^6$, sulfur or oxygen;

$R^6$ is hydrogen or alkyl;

$n^1$ is zero or 1;

F is linear or branched alkylene of 1–10 carbon atoms;

n is zero or 1, with the proviso that if $n^1$ is 1, n is 1 and if $n^1$ is 0, n is 0;

$R^3$ is

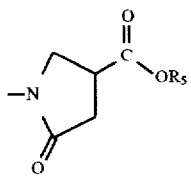

$R_5$ is alkyl or trialkylsilyl.

2. The organosilane and organosiloxane monomers as claimed in claim 1, wherein R are hydrolyzable groups selected from halogen, acyloxy, N,N-Dialkyl-aminoxy, N-alkylamido, monoalkylamino, dialkylamino, isocyanato, alkylthio or cyano groups or mixtures of the same.

3. The organosilane and organosiloxane monomers as claimed in claim 2, wherein $R^1$ is selected from substituted or unsubstituted lower alkyl, cycloalkyl, substituted or unsubstituted aryl, alkenyl, alkynyl or —OSi$(R^1)_3$.

4. The organosilane and organosiloxane mononers as claimed in claim 2, wherein $R_5$ is lower alkyl or trialkylsilyl.

5. The organosilane and organosiloxane monomers as claimed in claim 1, wherein n and $n^1$ are zero.

6. The organosilane and organosiloxane monomers as claimed in claim 2, wherein said compounds are an amphoteric class of organosilicone compounds, B is —NR$^6$ and $R^1$ is selected from substituted or unsubstituted alkyl, substituted or unsubstituted aryl, alkenyl, alkynyl or —OS$_i$(R)$_3$.

7. The organosilane and organosiloxane monomers aa claimed in claim 1, wherein $R^1$=—OSi$(CH_3)_3$ and x=1 to 3.

8. The organosilane and organosiloxane monomers as claimed in claim 7, wherein $R^2$ is methylene. $R^6$ is hydrogen or methyl, n=0 and $n^1$=0.

9. The method of preparing organosiloxane compounds having one or more pyrrolidone groups having functional carboxyl ester groups which comprises reacting a N-alkenyl pyrrolidone having a carboalkoxyl group of the formula:

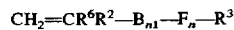

wherein:

$R^2$ is a linear or branched alkylene of 1–12 carbon atoms;

$R^6$ is hydrogen or alkyl;

F is linear or branched alkylene of 1–10 carbon atoms;

B is —NR$^6$, sulfur or oxygen;

$n^1$ is zero or 1;

n is zero or 1, with the proviso that if $n^1$ is 1, n is 1 and if $n^1$ is 0, n is 0;

$R^3$ is

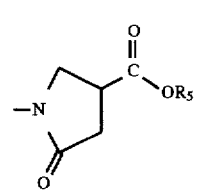

$R_5$ is alkyl or trialkylsilyl;

with an organosilane hydride group of the formula:

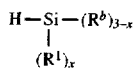

wherein:
$R^b$ is selected from a hydrolyzable group;
$R^1$ is selected from substituted or unsubstituted alkyl, cycloalkyl, substituted or unsubstituted aryl, aralkyl, alkeneyl, alkynyl or —O—Si—$(R^1)_3$ groups or mixtures of the same;
x is from 0 to 3;

at an elevated temperature in the presence of a noble metal catalyst for a time sufficient to react the hydride groups on the silicone atom with an olefinic group on the pyrrolidone.

10. The method of preparing organosiloxane compounds as claimed in claim 9, wherein $R^b$ are the same or different hydrolyzable group selected from halogen, alkoxy, alkoxyalkoxy acyloxy, N, N-Dialkylamoxy, N-alkylamido, monoalkylamino, dialkylamino, isocyanato, alkylthio, or cyano groups or mixtures of the same.

* * * * *